(12) United States Patent
Heikkilä

(10) Patent No.: US 11,083,370 B2
(45) Date of Patent: Aug. 10, 2021

(54) SINGLE-USE ELECTRODE PATCH

(71) Applicant: BITTIUM BIOSIGNALS OY, Kuopio (FI)

(72) Inventor: Ilkka Heikkilä, Oulu (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 112 days.

(21) Appl. No.: 16/482,415

(22) PCT Filed: Jan. 30, 2018

(86) PCT No.: PCT/EP2018/052242
§ 371 (c)(1),
(2) Date: Jul. 31, 2019

(87) PCT Pub. No.: WO2018/141732
PCT Pub. Date: Aug. 9, 2018

(65) Prior Publication Data
US 2020/0008675 A1   Jan. 9, 2020

(30) Foreign Application Priority Data

Feb. 2, 2017  (EP) ..................................... 17154367

(51) Int. Cl.
*A61B 5/00* (2006.01)
*A61B 5/1455* (2006.01)
(Continued)

(52) U.S. Cl.
CPC ........ *A61B 5/0006* (2013.01); *A61B 5/14551* (2013.01); *A61B 5/6833* (2013.01); *A61B 5/742* (2013.01); *A61B 5/01* (2013.01); *A61B 5/02055* (2013.01); *A61B 5/02455* (2013.01); *A61B 2560/0209* (2013.01)

(58) Field of Classification Search
None
See application file for complete search history.

(56) References Cited

U.S. PATENT DOCUMENTS

| 8,688,189 | B2 | 4/2014 | Shennib |
| 2006/0224072 | A1 | 10/2006 | Shennib |

(Continued)

FOREIGN PATENT DOCUMENTS

| WO | 2016/164623 | 10/2016 |

OTHER PUBLICATIONS

European Search Report for EP Application No. 17 15 4367 dated Aug. 1, 2017, 2 pages.
(Continued)

*Primary Examiner* — Brian T Gedeon
(74) *Attorney, Agent, or Firm* — Nixon & Vanderhye P.C.

(57) ABSTRACT

There is provided a method for measuring heart activity of a person in a single-use electrode patch, the method comprising: measuring the heart activity of the person; displaying the heart activity of the person on the basis of the measuring the heart activity; and broadcasting at least one message enabling transfer of heart activity data indicating the heart activity of the person from the electrode patch to the one or more external devices, wherein the broadcasting is performed while the heart activity of the person is being measured and displayed by the electrode patch.

14 Claims, 9 Drawing Sheets

(51) Int. Cl.
    *A61B 5/01*        (2006.01)
    *A61B 5/0205*    (2006.01)
    *A61B 5/0245*    (2006.01)

(56) References Cited

U.S. PATENT DOCUMENTS

| | | |
|---|---|---|
| 2006/0264767 A1 | 11/2006 | Shennib |
| 2007/0191728 A1 | 8/2007 | Shennib |
| 2009/0054737 A1* | 2/2009 | Magar ............... A61B 7/00 600/300 |
| 2011/0054286 A1 | 3/2011 | Crosby |
| 2012/0136265 A1 | 5/2012 | Kivistö |
| 2014/0128759 A1 | 5/2014 | Heikkilä |
| 2014/0324130 A1* | 10/2014 | Albrecht ............ A61N 1/0456 607/62 |
| 2017/0065823 A1* | 3/2017 | Kaib ................. A61B 5/0432 |

OTHER PUBLICATIONS

International Search Report for PCT/EP2018/052242 dated Apr. 9, 2018, 2 pages.
Written Opinion of the ISA for PCT/EP2018/052242 dated Apr. 9, 2018, 6 pages.

* cited by examiner

SINGLE-USE ELECTRODE PATCH

This application is the U.S. national phase of International Application No. PCT/EP2018/052242 filed Jan. 30, 2018 which designated the U.S. and claims priority to EP 17154367.1 filed Feb. 2, 2017, the entire contents of each of which are hereby incorporated by reference.

TECHNICAL FIELD

The invention relates to single-use electrode patches. More particularly, the present invention relates to electrode patches for measuring and displaying heart activity of a person.

BACKGROUND

Measuring vital signs of a person is common in a hospital or in an ambulatory environment. Often the number of persons is more than one or there may also be a need to apply multiple devices to a single person or a patient. As the number of monitoring devices increases, the used system may become increasingly complex to manage.

A disposable heart rate indicator is known from US 2012/0136265 which is herein incorporated in its entirety. However, as the number of electrode patches increases, there may be a need to find solutions that enhance the usability of the system utilizing one or more disposable heart rate indicators.

BRIEF DESCRIPTION

According to an aspect, there is provided the subject matter of the independent claims.

According to an aspect, there is provided a method for measuring heart activity of a person in a single-use electrode patch, the method comprising: measuring the heart activity of the person; displaying the heart activity of the person on the basis of the measuring the heart activity; and broadcasting at least one message enabling transfer of heart activity data indicating the heart activity of the person from the electrode patch to the one or more external devices, wherein the broadcasting is performed while the heart activity of the person is being measured and displayed by the electrode patch.

In an embodiment, the at least one message comprises heart activity data of the person.

In an embodiment, the method further comprises: determining medical status of the person at least on the basis of the measuring the heart activity, wherein the at least one message comprises data indicating the determined medical status of the person.

In an embodiment, the method further comprises: determining status of the electrode patch, wherein the at least one message comprises data indicating the determined status of the electrode patch.

In an embodiment, the method further comprises: receiving a control signal from an external device, wherein the broadcasting of the at least one message is initiated in response to receiving the control signal.

In an embodiment, the broadcasting the at least one message is performed using a first wireless communication circuitry of the electrode patch, and wherein the control signal is received using a second wireless communication circuitry of the electrode patch, the second wireless communication circuitry utilizing electromagnetic induction-based communication.

In an embodiment, the method further comprises: receiving a connection request from an external device in response to the broadcasting the at least one message; causing, on the basis of the connection request, establishment of at least one communication link between the electrode patch and the external device; and transmitting, by the electrode patch, heart activity data indicating heart activity of the person via the at least one communication link to the external device.

In an embodiment, the heart activity data transmitted via the at least one communication link comprises electrocardiography data.

In an embodiment, the method further comprises: detecting at least one predetermined event; and as a response to said detecting, initiating measuring and storing electrocardiography data of the person for a predetermined time.

In an embodiment, the method further comprises: measuring at least one of respiration rate of the person, temperature of the person, and oxygen saturation of the person.

In an embodiment, the method further comprises: initiating the broadcasting the at least one message in response to obtaining a control input, wherein the at least one message is configured to be broadcasted for a predetermined time.

In an embodiment, the method further comprises: stopping the broadcasting if a connection request is received from an external device or if the predetermined time has passed; and in response to the stopping the broadcasting, continuing to measure and display the heart activity of the person.

In an embodiment, the method further comprises: acquiring an input to initiate a training mode; in response to acquiring said input, preventing measurements by the single-use electrode patch; receiving simulation data from an external device; and displaying and broadcasting at least one vital parameter of a simulated person on the basis of the received simulation data.

According to an aspect, there is provided a single-use electrode patch comprising means for performing all the steps of the above described method.

According to an aspect, there is provide a system comprising a plurality of single-use electrode patches as described above; and a monitoring device comprising means for wirelessly receiving and displaying measurement data from the plurality of electrode patches.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which.

DETAILED DESCRIPTION OF SOME EMBODIMENTS

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1A:
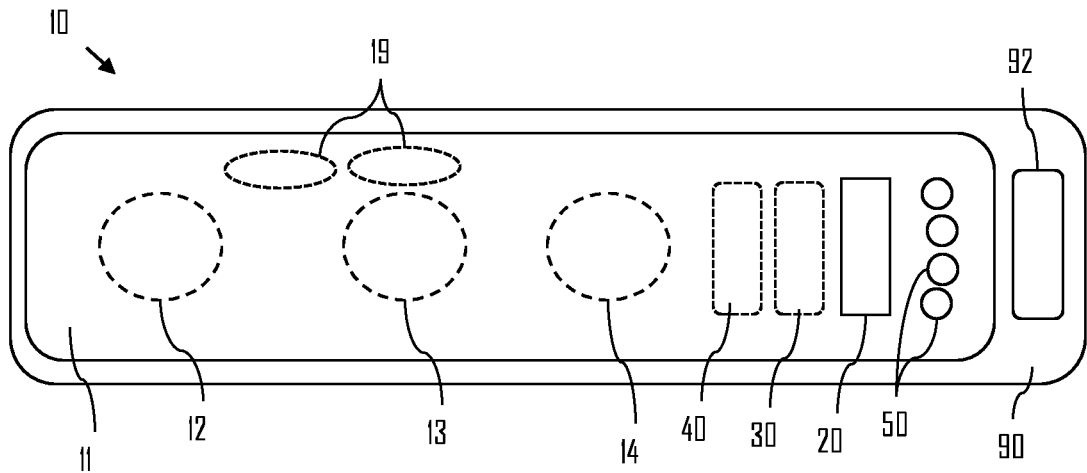
FIG. 1A illustrates a single-use electrode patch according to an embodiment.

FIG. 1A shows a single-use electrode patch 10 for measuring heart activity of a person. The term single-use means that in addition to being disposable, the electrode patch 10 is intended to be used only once and disposed after its use. So basically, once the single-use electrode patch 10 is attached to a person for monitoring the person and then removed once the monitoring is stopped, the patch 10 may be discarded (i.e. not used anymore). It is noted that reference hereinafter is made simply to patch or patch 10. This is simply due to efficiency reasons and such terms should be understood as referring to the single-use electrode patch 10. According to some embodiments, the single-use electrode patch 10 is a disposable electrode patch 10. In some embodiments, the patch 10 may be referred to as skin patch 10 as it may be used to monitor alternatively or additionally other vital signs of the person than heart activity.

Referring to an embodiment of FIG. 1A, the patch 10 comprises a base 11. The base 11 may comprise material or materials such as thermoplastic polymer (e.g. Acrylonitrile butadiene styrene (ABS)), thermoplastic polyurethane (TPU), fabric, rubber, plastic and/or leather. The base 11 may give the patch 10 a form that makes the patch 10 attachable to body tissue of a person. Thus, the base 11 may be made of one or more materials depending on the use case. According to an embodiment, the patch 10 is configured to be stretchable and/or elastic. For example, if the base 11 comprises stretchable and/or elastic material, the patch 10 may be stretchable and/or elastic. This may allow the patch 10 to have different attachment options when attached to a person (i.e. there may be, for example, different size persons: children and adults, which may require different placements). Such feature may increase the suitability of the same size patch 10 for monitoring persons having different dimensions. It may be especially beneficial to make the patch 10 stretchable and/or elastic such that it may be elongated in longitudinal direction as then the distance between two or more electrodes 12-14 may be increased, or decreased if first elongated. However, in some embodiment, the patch 10 is not necessarily stretchable or elastic.

As already indicated above, the patch 10 comprises at least two electrodes 12-14 for measuring heart activity of a person. In FIG. 1A, three electrodes are shown, but any two of the shown three would be enough for the measurement. However, using more than two electrodes 12-14 may enhance the measurement by making it more reliable. The electrodes 12-14 may be made of and/or comprise electrically conductive material. In an embodiment, the electrodes are wet electrodes, e.g. AgCl Electrocardiogram (ECG)-electrodes. The electrodes 12-14 may be disposed on an electrode foil, such as Polyethylene terephthalate (PET) foil.

In an embodiment, the size of the electrically exposed part of the electrodes is no more than 20 mm in diameter. In another embodiment, the dimensions of the electrically exposed part of the electrodes are no more than 20 millimeters (mm)×20 mm. In an embodiment, the electrically exposed part is substantially round. In such case the diameter of the electrically exposed part may be no more than 20 mm in some embodiments. The electrically exposed part may refer to part of the electrodes that is visible and configured to be in contact with the body tissue of the person (e.g. skin of the person).

The patch 10 may further comprise a display unit 20, 50 configured to display heart activity of the person on the basis of the measurements by the at least two electrodes 12-14. Thus, the electrodes 12-14 and the display unit 20, 50 may be electrically connected to each other via conductor element(s). There may be additional components therebetween, such as one or more processing units which are configured to determine or calculate heart activity parameter or value (e.g. heart rate, heart rate variation) based on the measurements by the at least two electrodes 12-14 and configured to cause the display unit 20, 50 to indicate or display the heart activity (e.g. the heart activity parameter or value) to the user.

In an embodiment, the display unit 20, 50 comprises a display 20. In an embodiment, the display unit 20, 50 comprises one or more light emitting elements 50 (e.g. light emitting diodes (LEDs)). Light emitting elements 50 may also be referred to as light emitters 50. In some embodiments, the patch 10 comprises both the display 20 and the light emitting elements 50. It is further noted that the display 20 may be based on, for example, LED technology. In some embodiments, the display 20 is a liquid crystal display (LCD). It is later described in more detail how the display unit 20, 50 displays or indicates different measurement results or values and parameter determined on the basis of measurement data.

Still referring to FIG. 1A, the patch 10 further comprises a communication circuitry 40. The communication circuitry 40 may enable wireless communication between the patch 10 and one or more external devices. The communication may be unidirectional, bidirectional and/or multidirectional. However, in an embodiment, the communication circuitry 40 at least supports wireless broadcasting.

The patch 10 may further comprise a controller 30 (may also be referred to as a controller circuitry 30). The controller 30 may be electrically connected to the at least two electrodes 12-14. Thus, the controller 30 may obtain measurement data using the at least two electrodes 12-14. Hence, when the patch 10 is attached to the body tissue of the person, the controller 30 may obtain measurement data (e.g. heart activity measurement data) of the person using the at least two electrodes 12-14. The controller 30 may then process the obtained measurement data. For example, a heart activity parameter or value (e.g. heart rate, heart rate variation) may be calculated on the basis of the measurement data. The controller 30 may further be electrically connected to the display unit 20, 50 (i.e. to the display and/or to the element(s) 50), and thus the heart activity parameter or value may be displayed to the user. In general, the patch 10 may comprise conductor element(s) (e.g. wiring) to connect the different elements 12-14, 40, 30, 20, 50 to each other such that the measurement data may be obtained, processed and further displayed in one form or another. Electrically connecting such elements to each other, when the used elements and their functions are described, may be clear to a skilled person.

Further, the electrode patch 10 comprises a power source 19. Power source 19 may be configured provide operating power to the electrodes 12-14, to the communication circuitry 40, to the controller 30, and to the display unit 20, 50. Hence, also the power source 19 may be electrically coupled to the elements of the patch 10 which require operating power in order to work.

The patch 10 may further comprise an amplifier operatively connected (i.e. electrically connected) to the at least two electrodes 12-14. The amplifier may be referred to as an ECG amplifier, for example. The amplifier may be configured to receive and amplify signals received from the electrodes 12-14. Thus, heart activity measurement and results may further be enhanced.

It is further noted that the amplifier, the controller 30, the display unit 20, 50 and/or communication circuitry or circuitries 40 may be comprised in a Printed Circuit Board Assembly (PCBA). Thus, the patch 10 may comprise the PCBA comprising at least one of the describe elements of the patch 10.

Additionally, the patch 10 may further comprise a protective liner 90 or liners. Such protective liner 90 may be configured to be removed before attaching the patch 10 to the person. The patch 10 may comprise an adhesive element (e.g. adhesive layer). Thus, in storage, the adhesive layer may remain in operational state for longer periods of time as the adhesive may not extensively evaporate during storage. Once the protective layer 90 is removed, the adhesive layer becomes visible, and thus the patch may be attached to the person. In an embodiment, the adhesive layer is situated between the base 11 and the removable protective liner 90. However, it could be situated on one or more edge areas of the patch 10. However, it may be beneficial to attach the electrodes 12-14 to the body tissue using adhesive in the area of the electrodes 12-14 in order to obtain more reliable connection and thus more reliable results. In some embodiments, the protective liner 90, also referred to as storage cover, may extend over at least one edge of the base 11. This may enable the protective liner 90 to be removed easily. In an embodiment, the protective liner 90 comprises at least one perforation or opening 92. The opening 92 may be situated on a part of the protective liner 90 that extends over the edge area of the base 11, as shown in FIG. 1A.

Figure 1B:
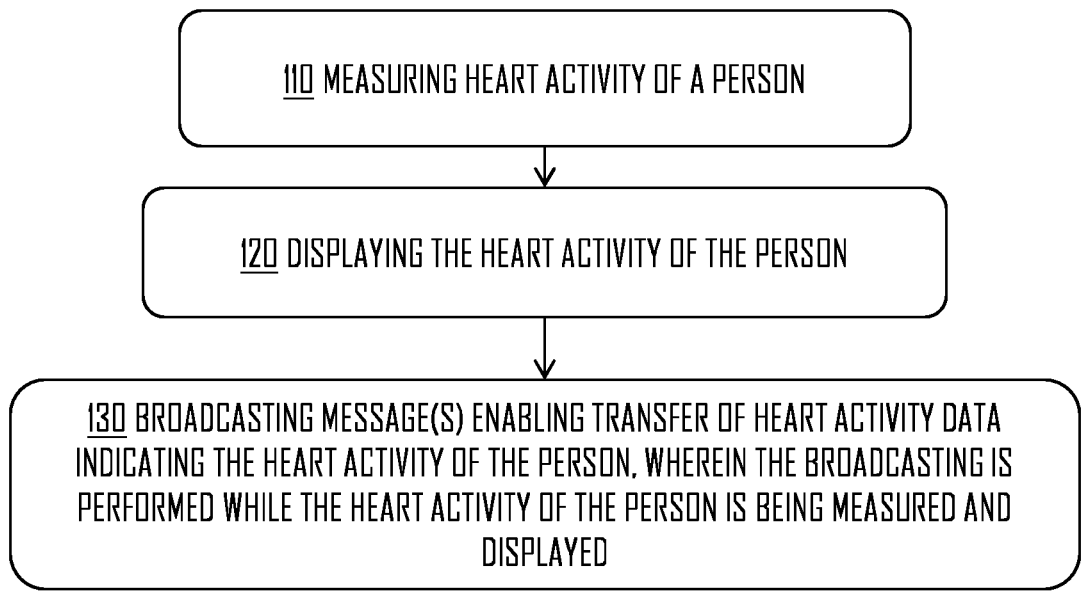
FIG. 1B illustrates a flow diagram of a method performed by a single-use electrode patch.

FIG. 1B illustrates a flow diagram according to an embodiment. Referring to FIG. 1B, a single-use electrode patch may measure heart activity of a person (step 110); display the heart activity of the person on the basis of the measuring the heart activity (step 120); and broadcast at least one message enabling transfer of heart activity data indicating the heart activity of the person from the single-use electrode patch to the one or more external devices, wherein the broadcasting is performed while the heart activity of the person is being measured and displayed by the single-use electrode patch (step 130). Thus, the heart activity data may be broadcasted at the same time or simultaneously with the measuring and displaying the heart activity.

According to an embodiment, said single-use electrode patch is the patch 10.

Such solution enables each of one or more patches 10 to first of all measure and display at least some heart activity of a person. Such functionality, as described, may be known from US2012/0136265. However, wireless connectivity enables measured data to be transmitted to external device(s). However, performing pairing (i.e. forming a device pair utilizing bidirectional communication) between each patch 10 of the system and a monitoring device, used to monitor data from each patch 10 (e.g. attached to person(s) (e.g. patients)), may require an excessive amount of radio resources which are not always available. For example, some radio communication technologies do not support pairing with more than one device. Thus, the monitoring device could only receive data from one patch 10, and possible other patches 10 would need to be monitored via the display units 20, 50. Such is not very efficient nor in the best interest of patient safety. Hence, the proposed solution provides a clear benefit over the known solutions by transmitting broadcast message(s) and at the same time continuing to measure and display the measured data. This allows (1) each patch 10 to be monitored using only one monitoring device and (2) enables the patches 10 to still indicate the measurement results using the local display unit 20, 50. So even if the option (1) fails (e.g. broadcast message does not reach the monitoring device), the option (2) is still available, and if option (1) works, the monitoring personnel do not need to be right next to the monitored person all the time or move between persons.

Figure 2A:
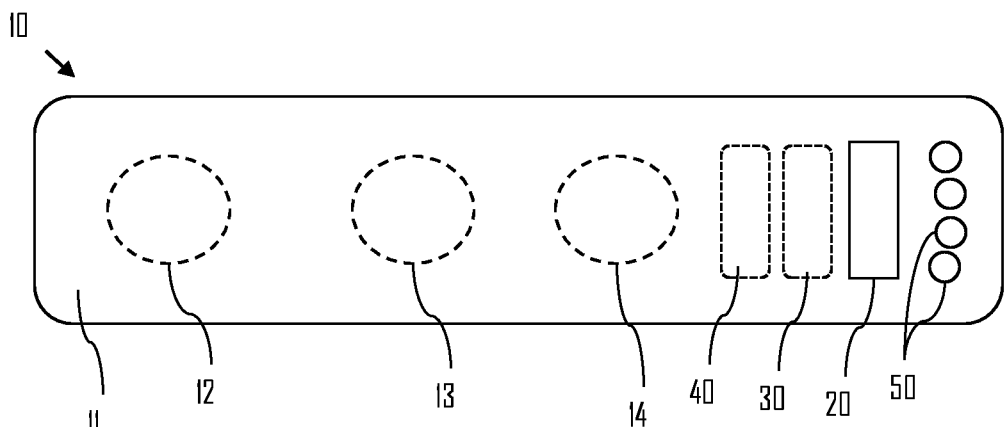
FIG. 2A illustrates a first side of a single-use electrode patch and FIG. 2B illustrates a second side of the single-use electrode patch according to an embodiment.
Figure 2B:
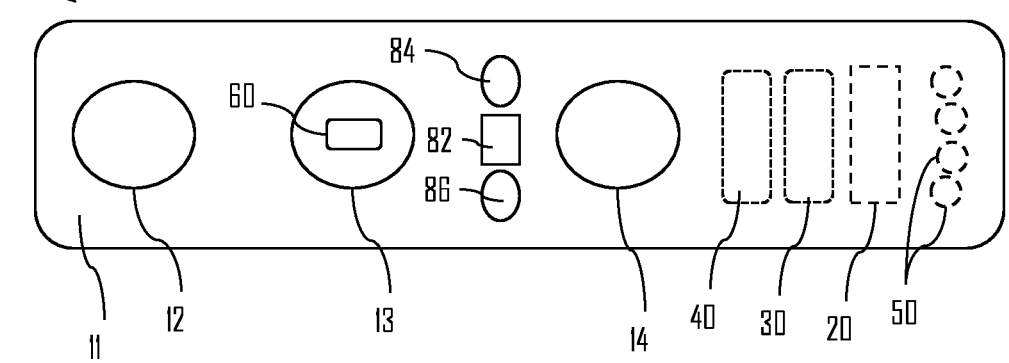
Figure 2C:
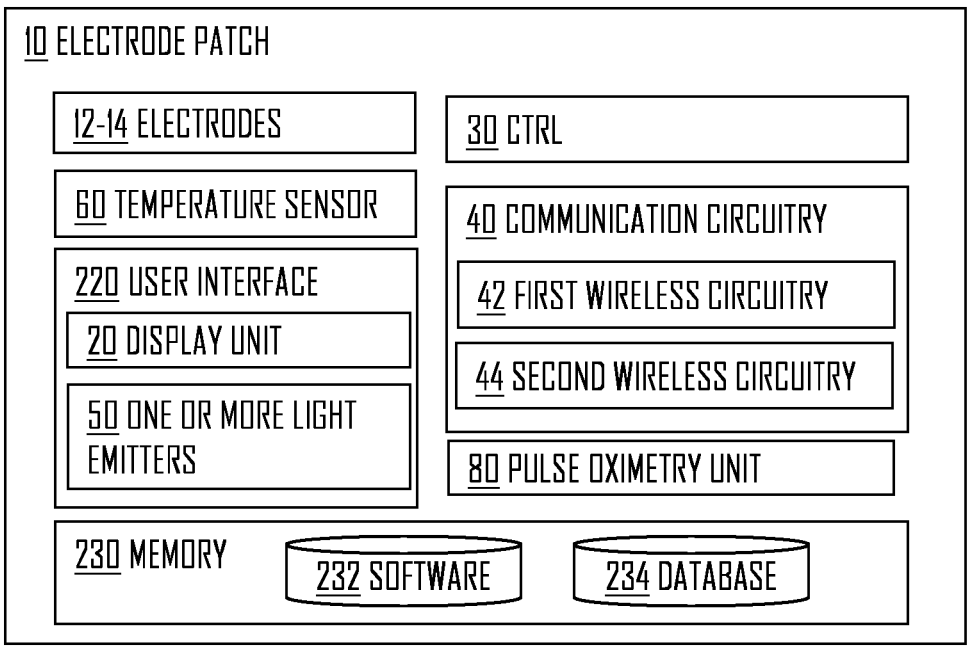
FIG. 2C illustrates a block diagram of a single-use electrode patch according to an embodiment.

Let us then look closer on some embodiments of the proposed solution. FIGS. 2A to 2C illustrate some embodiments. Referring first to FIG. 2A, a first side of the patch 10 is illustrated. The protective liner 90 is not shown in FIG. 2A, but could be used. That is, FIG. 2A may illustrate the patch 10 in a situation where the protective liner 90 is removed, for example. Alternatively, it may be situated on a second side of the patch 10, and thus may not be visible (and not extend over the edge area(s). Otherwise, the patch 10 of FIG. 2A may be similar to that illustrated and described with respect to FIG. 1A.

Going in a bit more detail, according to an embodiment, the electrodes 12-14 are fixedly situated at the base 11. That is, the electrodes 12-14 may be installed to the base 11 by means of adhesive or sewing, for example. The electrodes 12-14 may be at least partially visible on the second side (shown in FIG. 2B) of the patch 10, such that they may contact the body tissue when the patch 10 is used.

According to an embodiment, the display unit 20, 50 are situated at the base 11. For example, they may be fixedly installed to the base 11. The display unit 20, 50 may be fixed such that they are at least partially visible on the first side of the patch 10. This may mean that the display unit 20, 50 may be integrated in the base 11. That is, when the patch 10 is attached to the body tissue, the display unit 20, 50 may be visible and thus able to display information according to measurements.

According to an embodiment, the controller 30 and/or the communication circuitry 40 are situated at the base 11. For example, they may be fixedly installed to the base 11. For example, the controller 30 and/or the communication circuitry 40 may be disposed within the base 11. Thus, these parts 30, 40 may be protected against external forces as they may be situated totally within the base, for example.

Referring to FIG. 2B illustrating the second side of the patch 10 (i.e. opposite side to the first side shown in FIG. 2A), the electrodes 12-14 may now be seen on the base 11. According to an embodiment, the patch 10 comprises at least two electrodes 12-14 configured to perform ECG measurements (e.g. electrodes 12 and 14). According to an embodiment, the patch 10 comprises an electrode 13 configured to drive current to counteract common mode voltage variations (i.e. act as a Right Leg Drive-electrode).

According to an embodiment, the patch 10 further comprises at least one temperature sensor 60. The at least one temperature sensor 60 may be situated at least partially within the base 11. One suitable position may be the position of the third electrode 13 used to drive current to counteract common mode voltage variations. For example, the temperature sensor 60 may be integrated in the base 11 under the electrode 13. However, it may also be configured to contact the body tissue in some embodiments. The at least one temperature sensor 60 may be located at the electrodes 12, 14 alternatively or additionally in some embodiments. The at least one temperature sensor 60 may be configured to measure body temperature of the person. Thus, e.g. temperature data 350 may be produce by the patch 10.

According to an embodiment, the at least two electrodes 12-14 are configured to measure respiration rate of the person. This may be performed simultaneously as the heart activity measurement. Similarly, the respiration rate measurements may be processed by the controller 30 in order to determined or calculate respiration rate of the person based on the measurements. The respiration rate measurement may be based on impedance pneumography.

Still referring to FIG. 2B, the patch 10 further comprises an oxygen saturation measurement unit 80 comprising a first light emitter 84, a second light emitter 86 and a light detector 82. For example, the light emitters 84, 86 may be LEDs. The light detector 82 may be configured to detect light. For example, the light detector 82 may be a photodetector or a matrix detector. The light emitters 84, 86 may be configured to emit light on a first and second frequency areas respectively. That is, the first light emitter 84 may be configured to emit light having a first wavelength and the second light emitter 86 may be configured to emit light having a second wavelength. The first and second wavelengths may be different. That is, the color of light emitter by the emitters 84, 86 may be different. When the patch 10 attached to the person (e.g. patient), the emitters 84, 86 may emit light towards the body tissue (e.g. skin) of the person. The emitter light may travel within the tissue. At least some of the light may further propagate back towards the light detector 82 which may be configured to detect the light propagated in the tissue. Based on detected light by the detector 82, the controller 30 may determine oxygen saturation of the person. Thus, oxygen saturation data may be produced and/or the oxygen saturation may be displayed, for example. Oxygen saturation may be determined based on how much of the light having different wavelengths is received. That is, saturated blood may reflect light having a different wavelength than unsaturated blood. The light emitters 84, 86 and the detector 82 may be situated on the same side of the patch 10. The oxygen saturation measurement unit 80 may also be referred to as pulse oximetry unit 80 (as it is shown in FIG. 2C), for example.

Referring to FIG. 2C illustrating a block diagram of the patch 10, the patch 10 may comprise at least some of the elements described already above with reference to FIGS. 1A-2B. According to an embodiment, the communication circuitry 40 is configured to provide the electrode patch 10 data communication capability according to Bluetooth standard(s). Thus, the communication circuitry 40 may support Bluetooth Low Energy (BLE, sometimes referred to as Bluetooth Smart) and/or Bluetooth 5.0. According to an embodiment, the communication circuitry 40 is configured to provide the electrode patch 10 data communication capability according to Bluetooth, Wireless Local Area Network (WLAN), ANT, ANT+, and/or any other suitable communication technology. However, Bluetooth may be especially suitable for the broadcasting function (e.g. Bluetooth 4.2 or Bluetooth 5.0).

According to an embodiment, the electrode patch 10 comprises a first wireless circuitry 42 realizing Bluetooth communication capability and/or any other communication capability described above. Further, the electrode patch 10 may comprise a second wireless circuitry 44 realizing communication capability according to different communication standard(s) compared with the Bluetooth. One example of this may be electromagnetic induction-based communication. Example of such communication may be Near Field Communication (NFC) or some other communication method according to Radio Frequency Identification (RFID) specifications. For example, the first wireless circuitry 42 may be configured to perform the broadcasting the at least one message and the second wireless circuitry 44 may be configured to receive configuration message(s) from external device(s). The configuration message(s) may have an effect on the function of the patch 10 (e.g. what data is broadcasted and/or when).

According to an embodiment, the electrode patch 10 further comprises at least one memory 230. The at least one memory 230 may comprise software 232 implementing the functionality of the electrode patch 10. In an embodiment, the at least one memory 230 comprises a database 234 for storing measurement and/or configuration data. For example, heart activity data, temperature data, oxygen saturation data and/or respiration rate data may be stored into the memory 230 (e.g. in the database 234). So measurements by the at least two electrodes 12-14 the at least one temperature sensor 60, and/or the oxygen saturation measurement unit 80 may be obtained by the controller 30. The controller may process the measurements into data characterizing the measurements. The data or at least some of the data may be, for example, stored into the memory 230. Additionally or alternatively, the data or at least some of the data may be displayed using the display unit 20, 50. Additionally or alternatively, the data or at least some of the data may be transmitted using the communication circuitry 40 (e.g. the first wireless circuitry 42).

According to an embodiment, the patch 10 comprises a user interface 220. The user interface may comprise the display unit 20, 50 and/or one or more buttons or keyboards. For example, a touch-screen display can be utilized. The user interface 220 may be used to trigger some functionalities on the electrode patch 10. For example, the patch 10 may be turned on or off using the user interface 220. For example, the broadcasting the at least one message may be initiated using the user interface 220 (e.g. move from block 402 to block 408 of FIG. 4A by pressing a button of the user interface 220). Additionally, the broadcasting may be stopped using the same interface. That is, the patch 10 may start broadcasting according to a user input via the user interface 220. That is, the patch 10 may stop broadcasting according to a user input via the user interface 220.

Figure 3A:
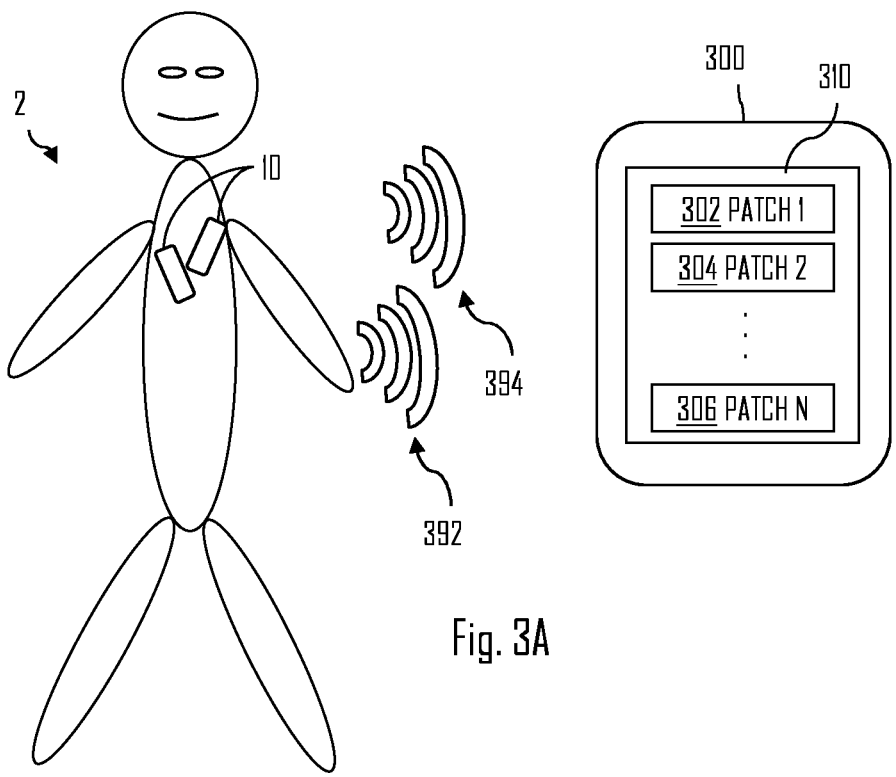
FIG. 3A illustrates a system according to an embodiment.
Figure 3B:
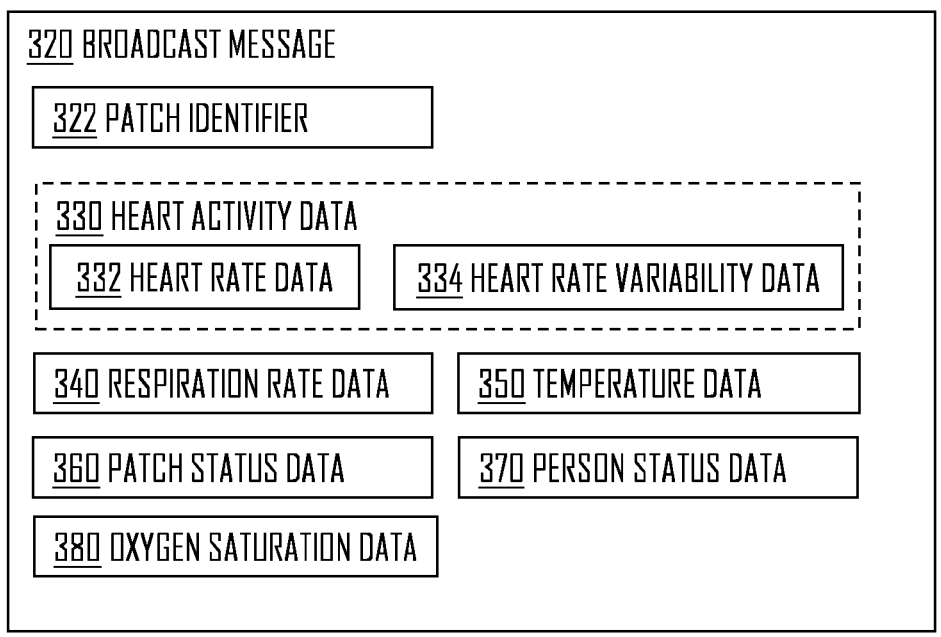
FIG. 3B illustrates a broadcast message according an embodiment.

According to an embodiment, the patch 10 comprises the pulse oximetry unit 80 (also referred to as oxygen saturation measurement unit). The unit 80 may comprise the emitters 84, 86 and the detector 82. Let us then look at some embodiments shown in FIGS. 3A to 3B. Referring first to FIG. 3B, the at least one message broadcasted by the patch 10 may be referred to as at least one broadcast message 320.

According to an embodiment, the broadcast message 320 comprises heart activity data 330 of the person. The heart activity data 330 may represent heart activity of the person measured using the at least two electrodes 12-14.

In an embodiment, the heart activity data comprises at least one of heart rate data 332 and heart rate variability data 334.

In an embodiment, the broadcast message 320 comprises patch identifier 322. The patch identifier may enable the patch 10 to be identified among a plurality of patches that may also perform broadcasting.

In an embodiment, the broadcast message 320 comprises respiration rate data 340. The respiration rate data 340 may represent respiration rate of the person measured using the at least two electrodes 12-14.

In an embodiment, the broadcast message 320 comprises temperature data 350. The temperature data 350 may represent body temperature of the person measured using the at least one temperature sensor 60.

In an embodiment, the broadcast message 320 comprises oxygen saturation data 380. The oxygen saturation data may indicate or represent oxygen saturation of the person measured using the oxygen saturation measurement unit 80.

In an embodiment, the patch 10 determines medical status of the person at least on the basis of the measuring the heart activity. The determination may be based on the heart activity data, the respiration rate data, oxygen saturation data and/or the temperature data. In an embodiment, the broadcast message 320 comprises person status data 370. I.e. the at least one broadcasted message may comprise data indicating the determined medical status of the person (i.e. the person status data 370). Alternatively or additionally, the display unit 20, 50 may indicate the status of the person. E.g. the display unit 20, 50 may indicate a warning if status of the person is determined, by the controller 30, to be critical.

The person status data, transmitted and/or displayed, may indicate the status of the person. Status of the person may comprise indicating that the person is OK or not OK, for example. For example, if heart rate is too low or too high, the status may be not OK. In such case the patch 10 may trigger an alarm which may be displayed on the display unit 20, 50 or on the monitoring device 300. For example, the alarm may be triggered if the heart rate of the person exceeds a threshold (e.g. is too low or too high).

In an embodiment, the patch 10 determines status of the patch 10. Status of the patch 10 may be indicated using the at least one broadcasted message. Additionally or alternatively, the display unit 20, 50 may indicate the status. In an embodiment, the broadcast message 320 comprises patch status data 360 indicating the status of the patch 10. For example, the status of the patch 10 may indicate battery level (i.e. power source status) and/or are the electrodes 12-14 connected properly. For example, the status may comprise indicating whether or not the patch 10 is able to perform the measurements. For example, if at least one of the electrodes 12-14 is not properly connected, the light emitter(s) 50 may so indicate (e.g. red light). However, if the electrodes are properly connected and the measurement may be performed, the light emitter(s) 50 may so indicate (e.g. green light). Similarly, the light emitter(s) 50 may indicate whether or not the radio of the patch 10 is active or not (e.g. broadcasting is on or off). For example, the patch status data may comprise remaining and/or passed operating time of the patch 10. For example, the patch status data may comprise a data packet counter indicator (e.g. how much data is broadcasted and/or transmitted). For example, the patch status data may comprise indication about noise.

According to an embodiment, the broadcast message 320 comprises patch identifier 322, heart activity data 330, respiration rate data 340, temperature data 350, oxygen saturation data 380, patch status data 360, and/or person status data 370.

In an embodiment, a first broadcast message 320 and a second broadcast message 320 are broadcasted subsequently. The first and second broadcast messages may comprise same type of data (e.g. heart rate), but possibly indicate a different value (i.e. heart rate changes between measurements). However, it may be possible that the first and second broadcast messages comprise different type of data. E.g. one broadcast message comprises heart activity data and the other respiration rate data. Thus, there may be different broadcast messages each comprising a different data fields, wherein each data field indicates a certain data field-specific parameter. For example, one data field is associated only with heart activity data. For example, another data field is associated only with respiration rate data. Similar logic may apply to all parameter or values indicated in the broadcast message 320 of FIG. 3B. Referring to FIG. 3A, a system comprising at least one patch 10 and a monitoring device 300 is shown. The system may comprise a plurality of patches 10. The patches 10 may be attached to one or more persons. I.e. there can be a plurality of patches attached to only one person 2. The person 2 may be an accident victim at an accident site, a patient at home or at a hospital, for example. The broadcasting the at least one message may be implemented with the radio waves 392, 394, wherein each patch 10 may independently broadcast data. The monitoring device 300 may comprise a wireless communication circuitry configured to receive the broadcasted message(s). Further, the monitoring device 300 may comprise a display 310 configured to display received data (i.e. received broadcasted message(s)) associated with patch 10 or patches 10. That is, the monitoring device 300 may display data 302-306 received from each patch 10 of the system. Thus, for example, heart activity data, temperature data, oxygen saturation data, and/or respiration rate data associated with a first patch may be displayed on the display 310 using a specific information element 302. Similarly, heart activity data, temperature data, oxygen saturation data, and/or respiration rate data associated with a second patch may be displayed on the display 310 using another specific information element 304. This may apply to all patches 10 from which data is received (e.g. N number of patches and N number of specific information elements 302-306, wherein N denotes a positive integer number). The specific information elements may be displayed on one view of the display and/or on a plurality of views. E.g. each patch 10 may be associated with a specific view such that data associated with only one patch is displayed at a time. For example, there may be a general view displaying all the patches and associated data. If one patch is selected, a more detailed view may be displayed, for example. For example, the overall view of all patches may simply indicate patch identifier and person status, whereas the detailed view may display heart activity data, respiration rate data, temperature data, oxygen saturation data, patch status and/or person status data.

Figure 4A:
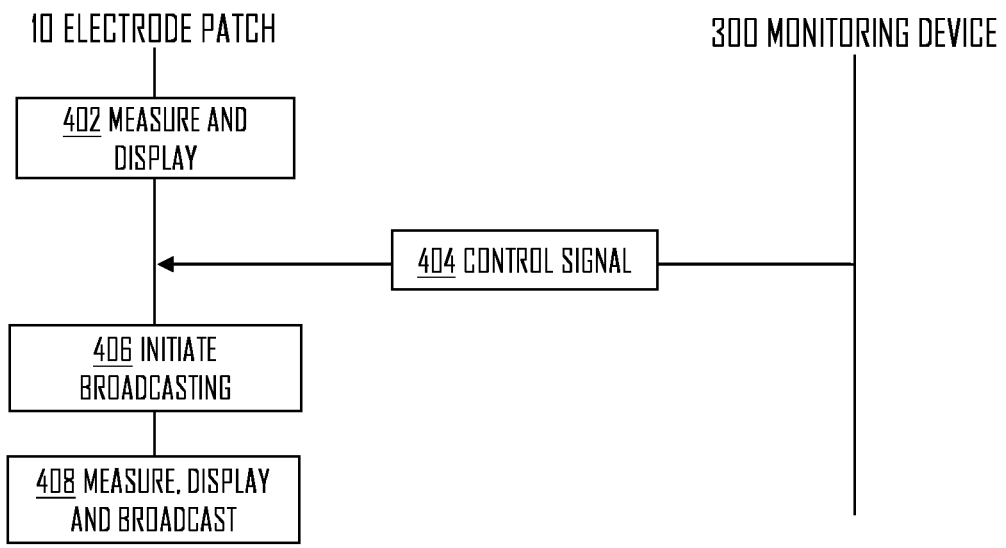
FIGS. 4A to 4C illustrate some embodiments.
Figure 4B:
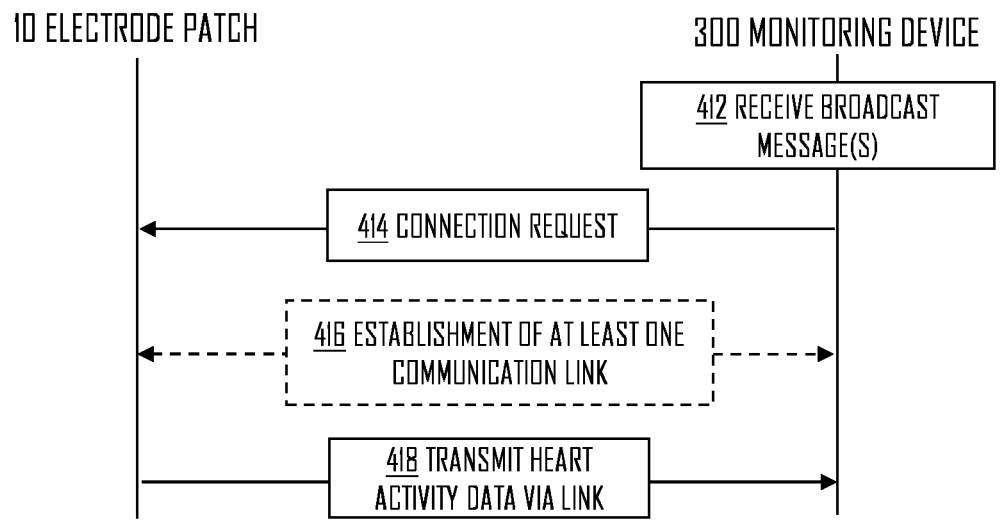
Figure 4C:
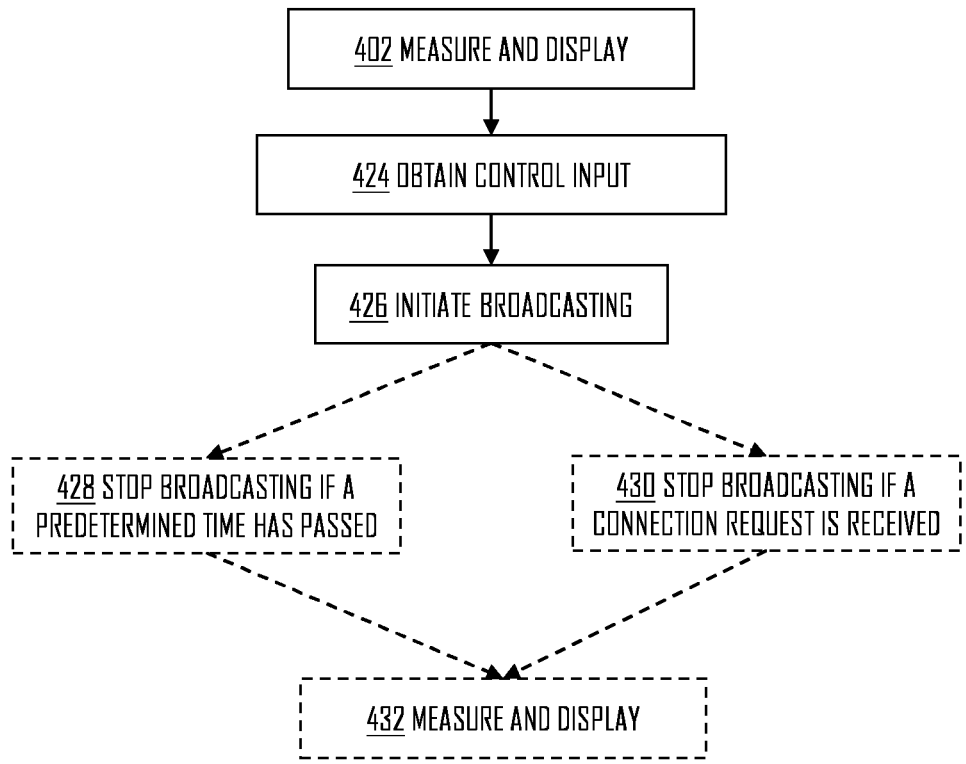

FIGS. 4A to 4C illustrate some embodiments. Referring to FIG. 4A, in block 402 the patch 10 may perform measurements and display the measurement data via the display unit 20, 50. Such data may comprise heart activity data, respiration rate data, oxygen saturation data, and/or temperature data, for example. The patch 10 may receive a control signal from an external device (e.g. the monitoring device 300) (block 404), wherein the broadcasting of the at least one message (block 406) is initiated in response to receiving the control signal. That is, the monitoring device 300 may transmit the control signal in block 404 which the patch 10 may receive and thus initiate the broadcasting. In block 408, the patch 10 may thus measure and display the data and further, at the same time, broadcast the at least one message

408. Hence, the monitoring device 300 may be able to receive the broadcasted at least one message. The control signal may be received via a wireless switch (e.g. NFC or similar switch). For example, a reed switch can be used, wherein the control signal may be understood as caused by a magnetic field of the monitoring device 300. So the control signal is not necessarily transmitted via air-interface, but it may be caused by an external device.

According to an embodiment, the broadcasting the at least one message is performed using the first wireless communication circuitry 42 of the patch 10. The control signal (block 404) may be received using the second wireless communication circuitry 44 of the patch 10, wherein the second wireless communication circuitry 44 may utilize electromagnetic induction-based communication. So the broadcasting may be initiated using an NFC switch, for example. In an embodiment, the broadcasting is performed according to Bluetooth standards. So, the at least one message may be referred to as at least one Bluetooth advertising message.

In an embodiment, the monitoring device 300 transmits a control signal to the patch 10 causing the patch 10 to stop the broadcasting. I.e. move from block 408 to block 402. Hence, the patch 10 may receive control signal(s) that either trigger the broadcasting or stop the broadcasting.

Referring to FIG. 4B, the monitoring device 300 may be configured to receive the broadcasted at least one message (block 412). It may be that the monitoring device 300 does not receive or successfully decodes all the messages, but only some due to interference or some other unideal conditions. However, it may listen certain radio band(s) to receive the broadcasted message (s). The monitoring device 300 comprises, in an embodiment, a Bluetooth circuitry. In an embodiment, the monitoring device comprises NFC circuitry or similar electromagnetic induction-based communication circuitry.

Figure 6A:
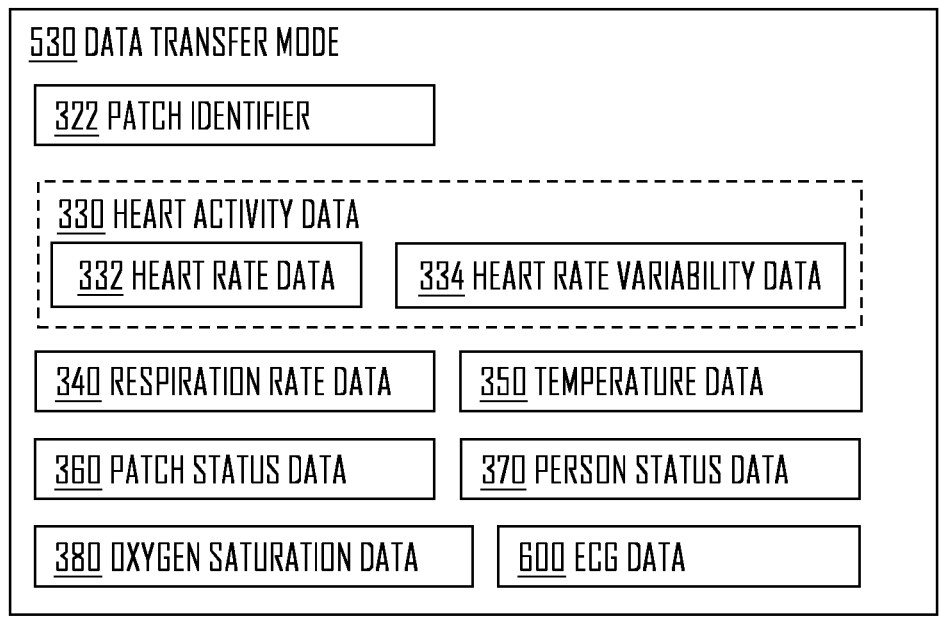
FIGS. 6A to 6B illustrate some embodiments.

In block 414, the patch 10 may receive a connection request from the external device (e.g. the monitoring device) in response to the broadcasting the at least one message (block 408 of FIG. 4A). In block 416, the patch 10 may cause, on the basis of the connection request, establishment of at least one communication link between the patch 10 and the external device. In block 418, the patch 10 may transmit heart activity data indicating heart activity of the person via the at least one communication link to the external device. The communication link may be additionally or alternatively utilized to transmit respiration rate data, oxygen saturation data, person status data, patch status data, and/or temperature data, for example. Any data that can be broadcasted (i.e. broadcast message 320) can also or alternatively be transmitted via the at least one communication link utilizing unidirectional communication. In general, using the communication link(s) larger amount of data can be transmitted compared with using the broadcasting. Examples of different data may be seen in an embodiment of FIG. 6A.

In an embodiment, the broadcasted messages comprise first type of heart activity data, and wherein the heart activity data transmitted via the at least one communication link comprises second type of heart activity data. For example, the first type and second type of heart activity data may differ from each other at least partly or totally. For example, the second type of heart activity data may be more detailed. For example, the broadcasting may enable transfer of heart activity data according to a certain bit rate, whereas the communication link may enable transfer of heart activity data with a higher bit rate. Hence, more detailed heart activity data may be transferred. I.e. more heart activity data may be transmitted in an equally long time period using the communication link than using the broadcasting.

In an embodiment, the second type of heart activity data indicates at least one different heart activity parameter of the person compared with at least one heart activity parameter indicated by the first type of heart activity data. For example, the second type of data may be more detailed and thus indicate, for example, an additional heart activity parameter. For example, if first type of heart activity data indicates or comprises heart rate, the second type of heart activity data may indicate or comprise heart rate and/or some other heart activity parameter, such as ECG parameter.

In an embodiment, the heart activity data transmitted via the at least one communication link comprises ECG data. ECG data may comprise, for example, ECG curve or curves. ECG data may require more radio resources than transmitting simply heart rate or heart rate variation data. Thus, it may be especially beneficial to establish the communication link(s) to transfer the ECG data from the patch 10 to the monitoring device 300. For example, let us consider a situation where the patch 10 broadcasts heart activity data comprising heart rate. The user of the monitoring device 300 may view the heart rate of the person (i.e. patient) on the monitoring device 300 as the monitoring device 300 may receive the one or more broadcasting messages indicating the heart rate. The user may decide that more detailed heart activity data is required. Hence, the monitoring device 300 may be used to transmit the connection request to the patch 10 and the communication link may be formed. Thus, the more detailed heart activity data (i.e. comprising ECG data, and possibly heart rate data and/or heart rate variation data) may be transferred using the communication link.

In an embodiment, once the ECG data is transmitted to the monitoring device, the at least one communication link is closed, and the patch 10 may resume normal operation. The normal operation may refer to either block 402 or block 408. For example, once the ECG data is transmitted, the patch 10 may determine that the at least one communication link is not needed anymore, and resume to perform operations of block 402 or block 408.

Figure 6B:
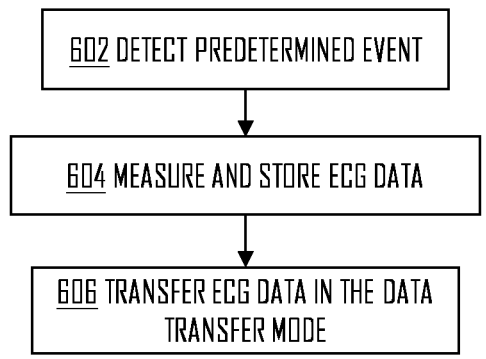

Referring to an embodiment of FIG. 6B, the patch 10 may detect at least one predetermined event (block 602); and as a response to said detecting, initiate measuring and storing ECG data of the person for a predetermined time (block 604). In block 606, the patch 10 may either using existing communication link or after receiving the connection request and establishing the connection (blocks 414, 416) transmit the ECG data to the monitoring device 300. So, the memory 230 of the patch may comprise ECG data from one or more periods, wherein at least some or all ECG data may be transmitted from the memory 230 to the monitoring device 300. The at least one predetermined event of block 602 may comprise receiving the connection request from the monitoring device. Hence, when the connection request is received, the patch 10 may start measure and store ECG data for a certain time period. Once measurement is performed for said time period, the ECG data may be transmitted to the monitoring device 300. Other events may include detecting, by the controller, a certain medical condition based on measurements using the at least two electrodes 12-14, the oxygen saturation measurement unit 80 and/or temperature sensor 60. For example, if heart rate, oxygen saturation, or temperature of the person is too low or too high, the ECG data measurement and storing may be triggered.

According to an embodiment, the ECG data is measured and stored for a predetermined time (e.g. 15-30 seconds) in block 604.

According to an embodiment, the monitoring device 300 requests the ECG data to be measured and stored for a certain time. The patch 10 may then measure and stored the ECG data for said certain time and then transmit said ECG data to the monitoring device 300.

Referring to FIG. 4C, in block 402 the patch 10 may measure and display measurement data. The patch 10 may obtain a control input (block 424) that causes the patch 10 to start broadcasting (block 426) while still continuing to measure and display measurement data. The control input may be a user input via the user interface 220 and/or a control signal from an external device, for example. In some embodiment, a person status condition, determined by the controller 30, may initiate the broadcasting. The broadcasting may be configured to continue for a predetermined time (e.g. 5, 10 or 60 seconds). Once the predetermined time has passed, the patch 10 may stop broadcasting (block 428) and resume to only measurement and displaying operations (block 432). However, the broadcasting may also be stopped if a connection request is received from an external device (block 430). This may be beneficial as the broadcasting may be unnecessary for the time period when the communication link(s) are used for data transfer. Once the required or requested data is transmitted to the external device, the patch 10 may continue to perform operations of block 432. In some embodiments, the block 432 comprises also the broadcasting. This may be beneficial when moving from block 430 to block 432.

Figure 5:
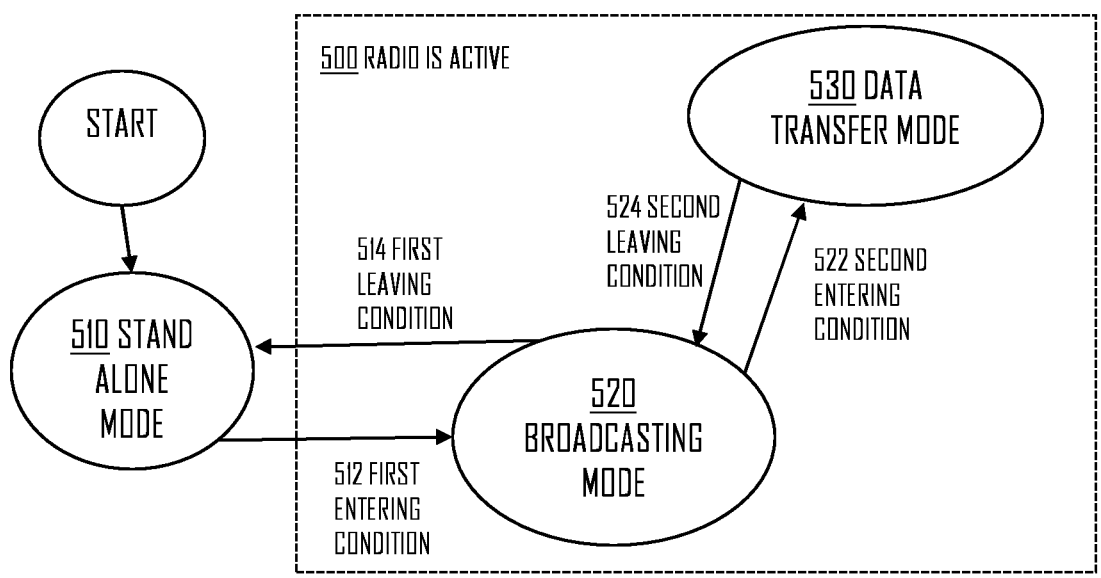
FIG. 5 illustrates states of a single-use electrode patch according to some embodiments.

Let us then look at an embodiment of FIG. 5 illustrating the described functionalities from a little bit different respective. Referring to FIG. 5, the patch 10 may be configured to be in a stand-alone mode 510 once the patch is activated. The activation may happen in response to removing the protective liner 90 from the patch 10. In an embodiment, the activation of the patch 10 is performed in response to removing a pin of the patch 10. The pin may be coupled with the power source 19, for example. Thus, when the pin is removed, the power source 19 may be activated or electrically connected to form an electric circuit with the elements of the patch 10 (e.g. electrodes 12-14, display unit 20, 50, controller 30, communication circuitry 40, temperature sensor 60, oxygen saturation measurement unit 80). The pin may be a part of the protective liner 90 or a separate of the protective liner 90. When the patch 10 is activated it may automatically turn on. Additionally, it may start to measure and display the measurement data (e.g. heart activity data). The first wireless circuitry 42 may be inactive (i.e. turned off) to conserve energy. In case the second wireless circuitry 44 is used, it may be configured to be active in case an active circuitry is used in order to receive control signals. However, the second wireless circuitry 44 may also be passive (e.g. passive NFC tag) which is activated via external energy. Thus, it may not necessarily require energy from the power source 19.

In response to fulfilling a first entering condition 512, the patch 10 may enter and operate in a broadcasting mode 520. In broadcasting mode 520, the patch 10 may perform actions of block 408, for example. Thus, when the first entering condition 512 is met, the first wireless circuitry 42 may be activated (i.e. radio is active 500 meaning that e.g. the Bluetooth may be active) and the broadcasting may start. The first entering condition 512 may be fulfilled if, for example, NFC signal is received or a user input via push-button of the user interface 220 is detected. Thus, for example, BLE advertising message(s) are configured to be transmitted, by the patch 10, for a predetermined time. The BLE advertising messages may comprise any of the data indicated in FIG. 3B.

In response to fulfilling a second entering condition 522, the patch 10 may enter and operate in a data transfer mode 530 in which, for example, ECG data is transmitted from the patch 10 to the external device (e.g. monitoring device) using at least one unidirectional communication link between said devices. I.e. the patch 10 may be paired with the monitoring device 300 for the data transfer. The data transfer may also utilize BLE communication including scan responses and scan requests, for example. The second entering condition 522 may be fulfilled if a connection request (e.g. ECG data request) is received from the monitoring device 300 by the patch 10. The connection request may be received via the first wireless circuitry 42, for example. The patch 10 may leave the data transfer mode 530 and return to broadcast mode 520 if a second leaving condition 524 is fulfilled. For example, the data transfer mode may be exited once the requested ECG data is transmitted to the monitoring device 300. During both the broadcasting mode and the data transfer mode, the measuring and displaying the heart activity data, respiration rate data, oxygen saturation data, and/or temperature data may continue by the patch 10. Thus, the measured data may be displayed at the same time on the monitoring device 300 and on the patch 10. In the mode 530 any of the data indicated in an embodiment of FIG. 6A may be transferred from the patch 10 to the monitoring device 300. The transferred data may depend on the data requested by the monitoring device 300 using the connection request (e.g. block 414).

It is also noted that the monitoring device 300 may obtain and display data associated with a plurality of patches 10 at the same time. The data may be obtained via broadcasted messages and/or via one or more communication links associated with one or more patches. So, the monitoring device 300 may be paired with one or more of patches 10 and at the same time receive broadcast message(s) from other devices.

The patch 10 may exit or leave the broadcasting mode 520 and return to stand-alone mode 510 if a first leaving condition 514 is fulfilled. For example, this may happen if the predetermined time (e.g. 5 seconds) has passed or if a connection termination signal is received from the monitoring device 300. In response, the first wireless circuitry 42 may be turned off or deactivated to conserve energy. In an embodiment, the passing of predetermined time (e.g. 5 seconds) does not trigger the leaving condition 514 if an acknowledgement (ACK) signal or message is received from the monitoring device 300 within said predetermined time period. Receiving such ACK message or signal may trigger the predetermined time period to restart. The ACK message or signal may be broadcasted by the monitoring device 300, for example, and thus each patch within range may receive it. ACK message may simply state that the monitoring device 300 is listening for broadcasted messages, and thus the patches 10 with active radio should continue the broadcasting. ACK message does not necessarily mean that the broadcasted message, by the patch 10, is received by the monitoring device 300. Actually, the patches 10 may broadcast the message(s) regardless whether or not the messages are received or not. For example, each broadcast message may indicate heart rate or some other measurement result or status for a certain time period (or single measurement result). Thus, even if one or more measurement results are not received by the monitoring device 300, the system may operate in a reliable manner, as the patches 10 may display the measurements or statuses on the display units 20, 50 and the monitoring device 300 may still receive at least some of the messages. So for example, if time between transmissions of two subsequent broadcast messages is 1 second and if one of three broadcast messages is not received, the time gap may increase from 1 second to 2 seconds between measurement data. So, the monitoring device 300 may still be able to display relevant information.

Figures 7A, 7B, 7C:
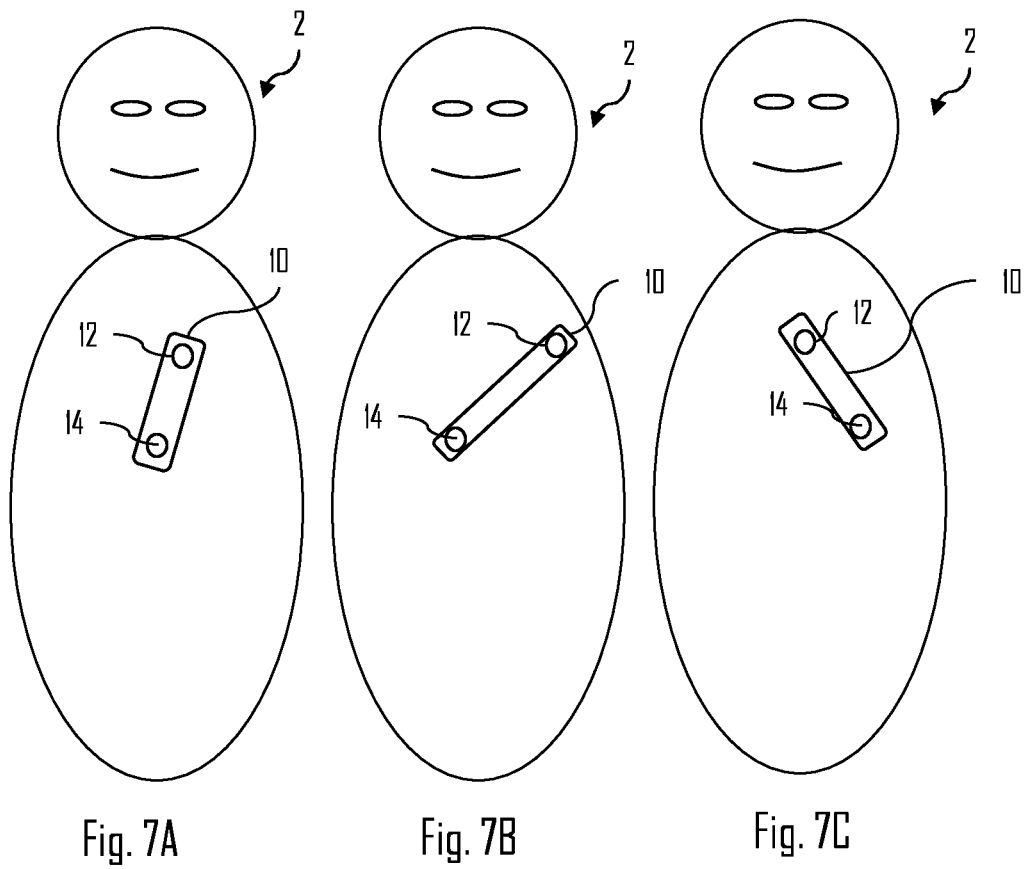
FIGS. 7A to 7D illustrate some embodiments.

FIGS. 7A to 7C illustrate some placement options for the patch 10 according to some embodiments. As described, according to an embodiment, the patch 10 is stretchable and/or elastic such that it allows the patch to be extended longitudinally in order to allow different patch placements. In FIG. 7A, an aVF connection may be shown, wherein the electrode 12 may provide negative electrode placement and the electrode 14 may provide positive electrode placement.

In FIG. 7B, a V1 connection may be shown, wherein the electrode 12 may provide negative electrode placement and the electrode 14 may provide positive electrode placement.

In FIG. 7B, a V5 connection may be shown, wherein the electrode 12 may provide negative electrode placement and the electrode 14 may provide positive electrode placement.

It needs to be understood that there may be a plurality of different connection options of which the V1, V5 and aVF are only few examples. As the patch 10 may be stretched, the different placement options may be enabled. For example, pregnant women may require the patch 10 to be able to stretch. Another example may be bra or bras used by women. In order to have the electrodes connected to the body tissue and such that the bras does not need to be removed (e.g. for chastity reasons), the patch 10 may be extended such that the electrodes 12, 14 are situated on different sides of the bras when attached to the skin of the person. There are numerous such examples, where the stretch and/or elastic properties may come handy.

The stretch and/or elastic properties of the patch 10 may derive from used materials. For example, the patch 10 may comprise rubber and/or elastic fabric or textile. In general, the base may be made of elastic material(s) or comprise elastic material.

Figure 7D:
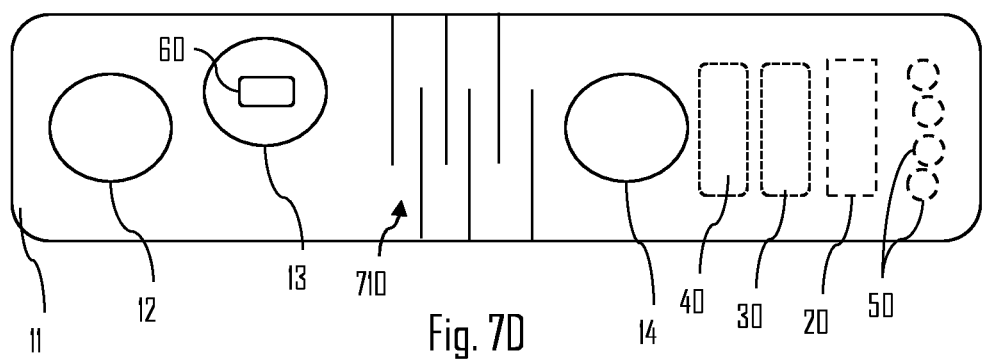

FIG. 7D illustrates an embodiment. Referring to FIG. 7D, in addition or alternative to the patch 10 comprising elastic and/or stretchable material, the patch 10 may comprise a plurality of cuts 710 enabling the patch 10 to be extended (i.e. longitudinally extended). Preferably the plurality of cuts 710 are situated between the electrodes 12 and 14 such that the distance between the two may be increased. When the patch 10 is longitudinally stretched, the cuts 710 may further open and thus extend the patch 10. Electrical connection between the elements that are situated on different sided of the cuts 710 may be achieved using wiring that is situated between the cuts 710 (i.e. circulates between the cuts). Another way may be to use conductive material in the base 11 at least in the area of the cuts 710. Thus, the base 11 may be a so called smart fabric or textile.

Let us further discuss the person status data 370 and related functionalities of the patch 10. In an embodiment, the patch 10 may be configured to monitor the measured data (e.g. heart activity data, respiration rate data, oxygen saturation data, and/or temperature data) and trigger an alarm signal if heart activity data of the person fulfills certain criterion or criteria. For example, the alarm signal may be triggered if heart rate of the person exceeds a certain threshold. That is, the heart rate is equal to and/or over a certain threshold (e.g. upper threshold). For example, the alarm signal may be triggered if heart rate of the person is equal to or below a certain another threshold (e.g. lower threshold). For example, if the patch 10 determines asystole and/or arrhythmia the alarm signal may be triggered. For example, the alarm signal may be triggered if body temperature of the person exceeds a certain threshold. That is, the temperature is equal to and/or over a certain threshold (e.g. upper threshold). For example, the alarm signal may be triggered if the temperature of the person is equal to or below a certain another threshold (e.g. lower threshold). For example, the alarm signal may be triggered if respiration rate of the person exceeds a certain threshold. That is, the respiration rate is equal to and/or over a certain threshold (e.g. upper threshold). For example, the alarm signal may be triggered if the respiration rate of the person is equal to or below a certain another threshold (e.g. lower threshold).

The alarm signal may cause a local alarm (i.e. at the device 10 using the display unit 20, 50 or one or more speakers of the user interface 220) and/or the alarm signal may cause an alarm indication to be transmitted to the monitoring device using the broadcasted message(s) or via the at least one communication link (i.e. when the patch 10 is paired with the monitoring device 300). The alarm indication or signal may be comprised in the person status data 370, for example. As described, the person status comprising the alarm(s) may also be stored to the memory 230 and transmitted to the monitoring device 300 when connection or broadcasting is available (i.e. radio is activated). This may not pre-empt local alarm(s).

In an embodiment, the triggered alarm signal causes the predetermined event of block 602 to be triggered or fulfilled. Thus, if the alarm signal is triggered, the ECG data measurement and storing may be initiated (block 604), and possibly transmitted to the monitoring device 300 (block 606).

In an embodiment, the display 20 is configured to display different measurement data in round robin way. That is, heart activity data, temperature data, respiration rate data, oxygen saturation data, person status data, and/or patch status data may be displayed using a round robin process.

Figure 8:
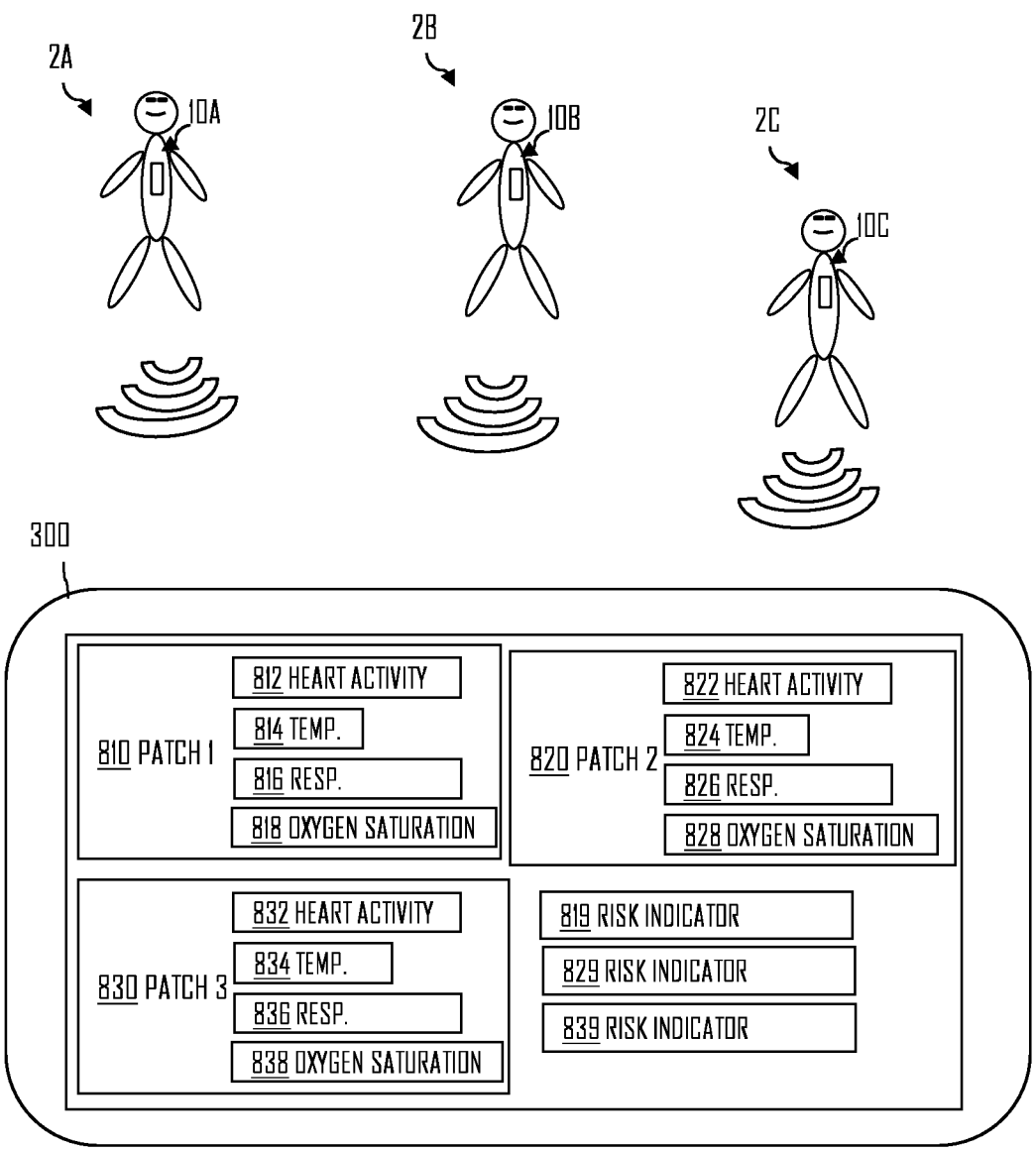
FIG. 8 illustrates a system comprising a monitoring device and a plurality of electrode patches according to an embodiment.

FIG. 8 illustrates yet another embodiment. In FIG. 8, a system comprising a plurality of patches 10 (e.g. 10A, 10B, 10C) and monitoring device 300 is shown. Referring to FIG. 8, in some embodiments, the patches 10 transmit (e.g. broadcast) data to the monitoring device 300. The monitoring device 300 may receive at least some of the broadcasted data and display it on its display. For example, displayed data may be associated with a patch such that the patch ID or patient ID (i.e. identifier) is shown with the data. The display data may comprise any data described in the various examples and embodiments above. For example, displayed data 810, by the monitoring device 300, for patch 10A may comprise heart activity 812, temperature 814, respiration rate 816, and/or oxygen saturation 818. For example, displayed data 820, by the monitoring device 300, for patch 10B may comprise heart activity 822, temperature 824, respiration rate 826, and/or oxygen saturation 828. For example, displayed data 830, by the monitoring device 300, for patch 10C may comprise heart activity 832, temperature 834, respiration rate 836, and/or oxygen saturation 838. There can be more than one patch per patient and more than three patches in the system.

According to an embodiment, the monitoring device 300 is configured to determine a risk parameter or score (e.g. early warning score) based on received data from a patch 10. That is, the risk parameter may be determined or calculated per person or per patch. The risk parameter determination may be based on the data received from the patch 10. For example, the risk parameter may be calculated based on heart activity data, temperature data, respiration rate data and/or oxygen saturation data. The risk parameter may be an estimation about the state of the person in the future. E.g. will the person be in OK condition after a certain time period. On the other hand, the risk parameter may indicate the current estimated state of the measured person. In a way it may be understood that the risk parameter or score is an estimation about the degree of illness of the person that is being measured that is based on the received data from the patch used to measure the person. The risk parameter calculation may be based on broadcasted data and/or data received via established communication link(s).

According to an embodiment, the monitoring device 300 indicates the risk parameter with a risk indicator 819, 829, 839. I.e. one risk indicator may indicate the risk parameter of a person or a patch. According to an embodiment, the monitoring device 300 performs an alarm based on the determined risk parameter. The alarm may comprise transmitting an alarm signal and/or outputting sound or visual output.

According to an embodiment, the risk parameter is determined based on at least two of the following: heart activity data, temperature data, respiration rate data, and oxygen saturation data. However, it may be beneficial to use more than two of the described to acquire even more accurate results.

Figure 9:
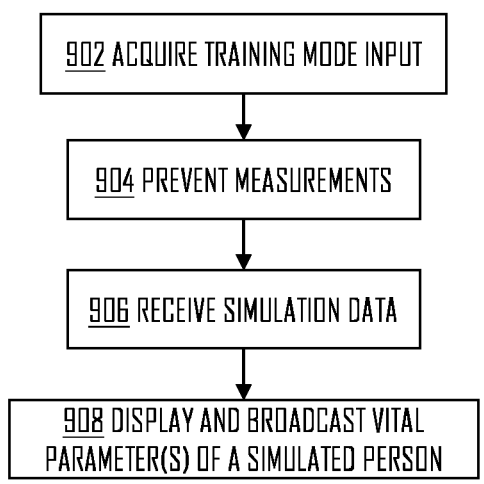
FIG. 9 illustrates a block diagram according to an embodiment.

FIG. 9 illustrates yet another embodiment. Referring to FIG. 9, the patch 10 may acquire an input to initiate a training mode (block 902). The input may be received via user interface of the patch 10 and/or via wireless communication with an external device (e.g. the monitoring device 300). In response to acquiring said input, the patch 10 may prevent measurements by the single-use electrode patch 10 (block 904). That is, the heart activity measurement, temperature measurement, respiration rate measurement and/or oxygen saturation measurement may be prevented. This may additionally mean that such measurement(s) is stopped if it already has started. Hence, the patch 10 may not measure any vital parameters of the person when the training mode is initiated.

In block 906, the patch 10 may receive simulation data from an external device. E.g. from the monitoring device 300 that may have also initiated the training mode on the patch 10. The patch 10 may then display and broadcast at least one vital parameter of a simulated person on the basis of the received simulation data (block 908). That is, the simulated data received from the external device may take the place of the measurement data (e.g. heart activity data (including heart rate and/or heart rate variability), respiration rate data, temperature data, patch status data, person status data, oxygen saturation data and/or ECG data). Thus, the external device may simulate patient conditions to the patch 10. Such may be very beneficial when training ambulatory personnel, for example.

In an embodiment, in block 908, the patch 10 relays simulation data received in block 906.

In an embodiment, said external device transmitting the simulation data to the patch 10 is different than the monitoring device 300. Thus, the monitoring device 300 may also be used by the training personnel and said external device by a teacher, for example. Said external device may be, for example, a computer, tablet computer or a smart phone, to name a few examples. In any case, said external device is an electronic device capable of wireless communication with the patch 10 or patches. It needs to be noted that the simulated conditions may be transmitted to a plurality of patches, thus simulating one or more persons.

In an embodiment, the patch 10 indicates that the training mode is active on the display unit 20, 50. This may happen in response to block 902, for example.

In an embodiment, the acquiring the training mode input (block 902) causes the patch to enter the training mode permanently.

In an embodiment, the simulation data comprises an ECG label associated with a certain ECG curve. The ECG curve may not be transferred among the simulation data. However, the patch 10 may transmit the ECG label in the training mode instead of the ECG data transmitted in the situations described above. The monitoring device 300 may then receive the ECG label and fetch a corresponding or associated ECG curve from its memory or from a database. Thus, the monitoring device 300 may display the associated ECG curve on its display on the basis of the ECG label.

It further needs to be noted that the simulation data may replace all the measurements performed by the patch 10, when the patch 10 is in the training mode initiated by the input of block 902. Hence, the embodiments described above may also be applicable to the training mode, wherein the measurement data is replaced by the simulation data. In an embodiment, the patch 10 or patches that are in the training mode may be referred to as slave devices and the external device providing the simulation data may be referred to as a master.

In an embodiment, the patch 10 further acquires an input to initiate operation mode when in the training mode. Accordingly, the patch 10 may then be configured to perform measurements as was described, for example, in FIG. 1B. Accordingly, the training mode may be exited.

According to an example embodiment, the patch 10 (or patches in case more than one patch is utilized) is configured to broadcast messages indicating the current heart activity of the person. In a similar manner, the patch 10 may be additionally or alternatively configured to display current heart activity of the person. The broadcasting and/or display of the current heart activity may be performed while the heart activity is measured. Further, the patch 10 may be configured to continuously measure the heart activity of the person and to continuously broadcast and/or display the current heart activity of the person which is acquired via the continuous measurement.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described in connection with FIGS. 1A to 9 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of FIGS. 1A to 9 or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments of FIGS. 1A to 9, or operations thereof. As explained above, the patch 10 may comprise the controller 30. The controller 30 may be realized using the at least one processor and the at least one memory including the computer program code. However, in some embodiments, the controller 30 may be realized using a specific circuitry, such as one or more Application Specific Integrated Circuitries (ASICs), which may be configured to perform the functions of the patch 10 accordingly.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 1A to 9 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium, for example. Coding of software for carrying out the embodiments as shown and described is well within the scope of a person of ordinary skill in the art. In an embodiment, a computer-readable medium comprises said computer program.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A method for measuring heart activity of a person in a single-use electrode patch, the method comprising:
   measuring the heart activity of the person;
   displaying on the electrode patch the heart activity of the person on the basis of the measuring the heart activity; and
   broadcasting messages enabling transfer of heart activity data indicating the heart activity of the person from the electrode patch to one or more external devices,
   wherein the broadcasting is performed while the heart activity of the person is being measured and displayed by the electrode patch,
   wherein said messages comprise heart activity data of the person;
   receiving a connection request from an external device in response to the broadcasting of the messages;
   causing, on the basis of the connection request, establishment of at least one additional communication link between the electrode patch and the external device; and
   transmitting, by the electrode patch, heart activity data indicating heart activity of the person via the at least one communication link to the external device.

2. The method of claim 1, further comprising:
   determining status of the electrode patch, wherein the messages comprise data indicating the determined status of the electrode patch.

3. The method of claim 1, further comprising:
   receiving a control signal from an external device, wherein the broadcasting of the messages is initiated in response to receiving the control signal.

4. The method of claim 3, wherein the broadcasting the messages is performed using a first wireless communication circuitry of the electrode patch, and wherein the control signal is received using a second wireless communication circuitry of the electrode patch, the second wireless communication circuitry utilizing electromagnetic induction-based communication.

5. The method of claim 1, wherein the broadcasted messages comprise first type of heart activity data, and wherein the heart activity data transmitted via the at least one communication link comprises second type of heart activity data.

6. The method of claim 5, wherein the second type of heart activity data indicates at least one different heart activity parameter of the person compared with at least one) heart activity parameter indicated by the first type of heart activity data.

7. The method of claim 1, wherein the heart activity data transmitted via the at least one communication link comprises electrocardiography data.

8. The method of claim 1, further comprising:
detecting at least one predetermined event; and
as a response to said detecting, initiating measuring and storing electrocardiography data of the person for a predetermined time.

9. The method of claim 1, further comprising:
measuring at least one of respiration rate of the person, temperature of the person, and oxygen saturation of the person.

10. The method of claim 1, further comprising:
initiating the broadcasting the at least one message in response to obtaining a control input, wherein the at least one message is configured to be broadcasted for a predetermined time.

11. The method of claim 10, further comprising:
stopping the broadcasting if a connection request is received from an external device or if the predetermined time has passed; and
in response to the stopping the broadcasting, continuing to measure and display the heart activity of the person.

12. The method of claim 1, further comprising:
acquiring an input to initiate a training mode;
in response to acquiring said input, preventing measurements by the single-use electrode patch;
receiving simulation data from an external device; and
displaying and broadcasting at least one vital parameter of a simulated person on the basis of the received simulation data.

13. A single-use electrode patch comprising at least one processor and at least one memory including the computer program code configured to cause the electrode patch to perform steps comprising:
measuring the heart activity of the person;
displaying on the electrode patch the heart activity of the person on the basis of the measuring the heart activity; and
broadcasting messages enabling transfer of heart activity data indicating the heart activity of the person from the electrode patch to the one or more external devices,
wherein the broadcasting is performed while the heart activity of the person is being measured and displayed by the electrode patch,
wherein said messages comprise heart activity data of the person;
receiving a connection request from an external device in response to the broadcasting the messages;
causing, on the basis of the connection request, establishment of at least one additional communication link between the electrode patch and the external device; and
transmitting, by the electrode patch, heart activity data indicating heart activity of the person via the at least one communication link to the external device.

14. A system comprising:
a plurality of single-use electrode patches according to claim 13;
a monitoring device comprising means for wirelessly receiving and displaying measurement data from the plurality of electrode patches.

* * * * *